United States Patent [19]

Kerb et al.

[11] 4,097,678
[45] Jun. 27, 1978

[54] $\Delta^{9\,(11)}$-5α-D-HOMO-20-KETO STEROIDS

[75] Inventors: Ulrich Kerb; Rudolf Wiechert; Otto Engelfried, all of Berlin, Germany

[73] Assignee: Schering Aktiengesellschaft, Berlin and Mergkamen, Germany

[21] Appl. No.: 693,847

[22] Filed: Jun. 8, 1976

[30] Foreign Application Priority Data

Jun. 11, 1975 Germany .............................. 2526372

[51] Int. Cl.$^2$ ............................................. C07J 63/00
[52] U.S. Cl. ...................... 560/257; 204/158 HA;
260/408; 260/410; 260/456 R; 260/586 E;
260/946; 560/1; 560/56; 560/61; 560/71;
560/73; 560/100; 560/105; 560/107; 560/122;
560/123; 560/124; 560/125; 560/180; 560/184;
560/185; 560/186; 560/188; 560/192; 560/194;
560/227; 560/228
[58] Field of Search .......... 260/488 B, 586 E, 476 C;
560/257, 107

[56] References Cited
U.S. PATENT DOCUMENTS 3,939,193  2/1976  Aleg et al. ...................... 260/488 B

OTHER PUBLICATIONS

Breslow et al., J.A.C.S., 96(1974), 1973.
Ibid 96 (1974), 6791.

Primary Examiner—Vivian Garner
Attorney, Agent, or Firm—Millen & White

[57] ABSTRACT

3α-Hydroxy and 3α-acyloxy- $\Delta^{9(11)}$-5α-D-homo-20-ketopregnenes of the formula

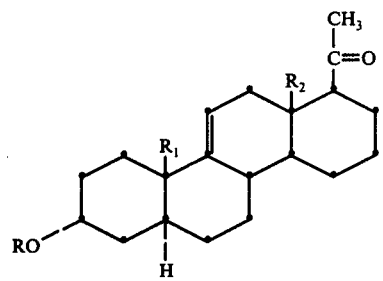

wherein R is hydrogen or acyl, $R_1$ is hydrogen or methyl and $R_2$ is methyl or ethyl, are produced by esterifying a corresponding 3β-hydroxy-5α-20-keto pregnane of the formula

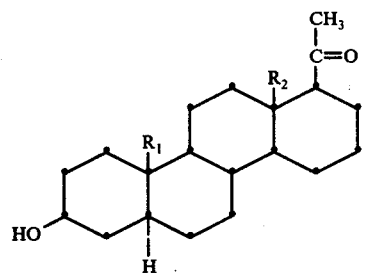

wherein $R_1$ and $R_2$ have the values given above, with m-iodo-benzoic acid with inversion of the 3β-oxy group to a 3α-oxy group; chlorinating the thus-produced 3α-m-iodobenzoyl ester with dichloroiodobenzene under irradiation; and treating the reaction product with a dehydrohalogenating silver salt. Optionally thereafter, the 3α-iodobenzoyl group is split off in a conventional manner to produce the corresponding 3α-hydroxy steroid and optionally the thus-produced 3α-hydroxy steroid is esterified to produce a desired 3-ester thereof.

11 Claims, No Drawings

$\Delta^{9(11)}$-5α-D-HOMO-20-KETO STEROIDS

BACKGROUND OF THE INVENTION

This invention relates to a novel process for the production of 3α-hydroxy- $\Delta^{9(11)}$-5α-D-homo-20-ketopregnenes and their esters.

It is known from the works by Breslow et al., e.g., J. Amer. Chem. Soc. 96 (1974) 1973; ibid. 96 (1974) 6791, that it is possible, in case of steroids esterified in the 3α-position, to chlorinate the tertiary $C_5$, $C_9$ and $C_{14}$ carbon atoms with dichloroiodobenzene under the influence of light and then split off hydrogen chloride again with the formation of a double bond at these positions.

However, this process has the disadvantage that it is applicable solely to those steroids which have no free carbonyl groups, such as 20-ketopregnanes.

In the process of this invention, 9α-chloro-D-homo-20-ketopregnanes are selectively produced from which hydrogen chloride is subsequently split off with a silver salt in a conventional manner to form a $\Delta^{9(11)}$-double bond.

SUMMARY OF THE INVENTION

In a composition aspect, this invention relates to novel 3α-hydroxy- and 3α-acyloxy- $\Delta^{9(11)}$-5α-D-homo-20-ketopregnenes of general Formula I

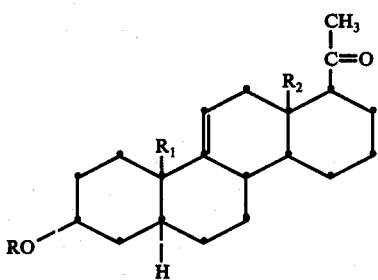

wherein R is hydrogen or acyl, $R_1$ is hydrogen or methyl and $R_2$ is methyl or ethyl.

In a process aspect, this invention relates to a process for their production comrpising the steps of esterifying a 3β-hydroxy-5α-D-homo-20-ketopregnane of general Formula II

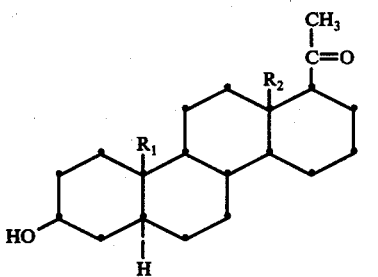

wherein $R_1$ and $R_2$ have the values given above, with m-iodobenzoic acid with inversion of the 3β-oxy group to a 3α-oxy group; chlorinating the thus-produced 3α-m-iodobenzoyl ester with dichloroiodobenzene under irradiation; and treating the reaction product with a dehydrohalogenating silver salt. Optionally thereafter, the 3α-iodobenzoyl group is split off in a conventional manner to produce the corresponding 3α-hydroxy steroid and optionally the thus-produced 3α-hydroxy steroid is esterified to produce a desired 3-ester thereof.

DETAILED DISCUSSION

Examples of contemplated compounds embraced by Formula I are those wherein:

(a) R is H;
(b) R is acyl;
(c) $R_2$ is $CH_3$, including those of (a) and (b);
(d) $R_2$ is $C_2H_5$, including those of each of (a) through (b);
(e) $R_1$ is H, including those of each of (a) through (d);
(f) $R_1$ is $CH_3$, including those of each of (a) through (d);
(g) R is H, including those of each of (a) through (f);
(h) R is m-iodobenzoyl, including those of each of (a) through (f); and
(i) R is alkanoyl of 1-6 carbon atoms, including those of each of (a) through (f).

It is surprising that in the process of this invention chlorination occurs selectively at the 9-position, since U.S. Pat. No. 2,681,353 teaches that dichloroiodobenzene leads in the case of 20-ketopregnanes quantitatively to 21-chloro-20-ketopregnanes.

The process of this invention is a multistage process which is preferably conducted without isolating and/or working up the intermediate reaction products.

In the first reaction stage, the 3β-hydroxy group of the starting steroid of general Formula II is inverted in a conventional manner and desirably esterified at the same time.

The inversion of the 3β-hydroxy compounds to the 3α-form can be conducted in accordance with conventional isomerization methods. For example, 3α-hydroxy-D-homo-19-nor -5α-pregnan-20-one can be produced from 3β-hydroxy-D-homo-19-nor-5α-pregnan-20-one via their 3β-mesyloxy-, 3β-tosyloxy or other sulfonyloxy ester, which ester is then treated with a known inverting agent, e.g., lithium acetate under heating, and subsequently the 3-ester is hydrolyzed, e.g., with potassium hydroxide solution to regenerate the free 3-hydroxy group.

In a preferred embodiment, the 3β→ 3α-isomerization of the 3-hydroxy group is conducted with simultaneous esterification thereof, for example, 3β-hydroxy-5α-D-homo-pregnan-20-one in a suitable solvent with a triaryl or trialkyl phosphine, e.g., triphenyl- or tributylphosphine, in the presence of the diethyl ester of azodicarboxylic acid and in the presence of the desired acid, such as, for example, m-iodobenzoic acid, to produce 3α-m-iodobenzoyl-5α-D-homo-pregnan-20-one. Suitable solvents are those inert relative to the reactants, e.g., tetrahydrofuran and dioxane. For a reference describing such inversion reaction, see Tetrahedron Letters 1973, p. 1619.

In the second reaction stage, the thus-produced 3α-acyloxy-D-homo-20-ketopregnane is photochemically halogenated with dichloroiodobenzene (phenyliodide dichloride) in a solvent. Suitable solvents are those which are not attacked by the halogenating agent employed, such as, for example, halogenated hydrocarbons, e.g., methylene chloride and chloroform, and aromatic hydrocarbons, e.g., benzene, chlorobenzene and toluene, and mixtures with one another. The introduction of an inert gas, such as, for example, nitrogen or argon, is advantageous during the reaction.

The photochemical reaction is induced by means of an ordinary sunlamp. For references describing the type of irradiation which can be used, see, e.g., J.Amer.-Chem.Soc. 96(1974)6791; ibid. 97(1975)6580.

In the third reaction stage, the thus-prepared 9α-halogen compound is treated in the homogeneous phase with a dehydrohalogenating silver salt, e.g., silver perchlorate, nitrate, acetate, or other silver salt soluble in the reaction solvent, whereupon the 9α-chlorine atom is split off as the insoluble silver chloride and is precipitated, with the formation of the $\Delta^{9(11)}$-double bond. Solvents which permit operation in an homogeneous phase are those in which the silver salt is soluble, such as, for example, acetone, acetic acid and water, and/or mixtures thereof. There is thus produced a compound of Formula I wherein R is acyl.

Optionally, a fourth reaction stage can follow the above-described states wherein the 3α-acyloxy group is split off in a conventional manner to produce a compound of Formula I wherein R is H. Especially suitable is alkaline saponification, e.g., employing a methanolic potassium hydroxide solution.

Optionally, a fifth reaction stage can follow, wherein the free 3α-hydroxy group is re-esterified in a conventional manner to form the desired final 3-ester group. A preferred method is the reaction with a reactive acid derivative in the presence of an alkaline reagent, such as, for example, the reaction with an acid chloride or acid anhydride in the presence of pyridine.

In addition to m-iodobenzoyl, in the compounds of Formula I, R can be the acyl radical of an alkanoic acid of up to 6 carbon atoms, e.g., acetyl, propionyl, butyryl and isobutyryl, as well as pivaloyl, formyl, pentanoyl, 2-methylbutyryl and hexanoyl. Contemplated equivalents of these alkanoyl esters are 3-esters of higher alkanoic acids, e.g., of 7-16 carbon atoms and other saturated, unsaturated, branched and polybasic carboxylic acids, including those substituted in the usual manner, for example, by hydroxy or halogen atoms; as well as of cycloaliphatic, mixed aromatic-aliphatic (alkaryl and aralkyl) acids, which can likewise be substituted in the usual manner. Examples of such contemplated equivalent esters are esters of triethylacetic, enanthic, octanoic, undecyclic, oleic and palmitic acid, cyclic acids, e.g., cycloaliphatic acids, containing, e.g., 5-18 carbon atoms, e.g., cyclopropylideneacetic, cyclobutylcarboxylic, cyclopentylcarboxylic, cyclopentylacetic, cyclohexylacetic, β-cyclopentylpropionic and β-cyclohexylpropionic acid, aroyl acids, e.g., mono or bicyclic aryl carbocyclic acid of 6-18 carbon atoms and 1 to 5, preferably 1 or 2 rings, e.g., benzoic o-, m- or p-methylbenzoic, o-, m- or p-fluorobenzoic, o-, m- or p-chlorobenzoic, α-naphthoic, β-naphthoic, 2,3-, 2,4-, 2,5-, 2,6-, 3,4- and 3,5-dimethylbenzoic, ethylbenzoic, 2,3,6-trimethylbenzoic and 3-methyl-α-naphthoic acid; an aralkyl acid, e.g., containing 7 to 18 carbon atoms, e.g., phenylacetic, β-phenylpropionic, a polybasic acid, e.g., containing 2-18 carbon atoms and 1 to 5 hydroxy groups, e.g., glycolic, lactic, citric, tartaric, d-maleic, succinic, d-glyceric and salicyclic acid; and the corresponding acids containing one, two or more of simple substituents, e.g., halo, alkoxy, acyloxy, etc., in the molecule, e.g., chloroacetic, fluoroacetic, dichloroacetic, trichloroacetic, trifluoroacetic, 2,3,4-trimethoxybenzoic, phenoxyacetic and α-naphthoxyacetic acid. Also contemplated as equivalents are 3-esters of sulfonic, e.g., methanesulfonic and p-toluenesulfonic, and phosphoric acids.

The compounds of general Formula I which can be produced according to the process of this invention are useful intermediates for the preparation of pharmacologically valuable compounds. The thus-prepared compounds are 11β-hydroxy and 11-oxo-D-homo-20-ketopregnanes having CNS-depressant activity, for reference see co-pending patent application Ser. No. 528,328 filed Nov. 29, 1974, now U.S. Pat. No. 4,045,574.

They are prepared by reacting the compounds of Formula I with N-bromosuccinimide in an aqueous solution of dioxane to the halohydrin and heating the 9α-bromo-11β-hydroxypregnane dissolved in tetrahydrofuran with tributyltin hydride in the presence of azodiisobutyronitrile.

The corresponding 11-oxo compounds are prepared by oxidation of the 11β-hydroxy compound employing chromic acid in a suitable reaction medium, e.g., glacial acetic acid or sulfuric acid/acetone or pyridine/methylene chloride.

In our concurrently-filed application Ser. No. 693,848, whose disclosure is incorporated herein by reference, we claim pregnenes otherwise corresponding to the D-homo-pregnenes of Formula I and the process for preparing them otherwise corresponding to the herein claimed process.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

PREPARATION

The 3β-hydroxy-D-homo-19-nor steroids employed as starting materials in the process of this invention can be prepared as illustrated below.

3β-Hydroxyestran-17-one is ethynylated in a conventional manner. (German Pat. No. 1,096,354; J. Org. Chem. 25 [1960] 1974; U.S. Pat. No. 3,084,173.) The thus-obtained 3β,17β-dihydroxy-17α-ethynylestrane is then converted into the corresponding 16-dehydro steroid by a conventional method. (German Unexamined Laid-Open Application DOS 1,593,521.) After introduction of the 17-pregnane side chain according to conventional methods (Helv. 26 [1943] 1004; DOS 1,668,688), the $\Delta^{16}$-19-nor-20-ketopregnane which is obtained is reacted to the corresponding 16α,17-methylene steroid, for example, according to the Corey method (E.J. Corey and M. Chaykovsky, J. Am. Chem. Soc. 84 [1962] 867; ibid. 84 [1962] 3782). From the saturated 16α,17-methylene steroid, the $\Delta^{17}$-unsaturated D-homo-19-nor steroid is then produced in a conventional manner by ring expansion (DOS 1,135,903).

1.1 g. of 3β-hydroxy-D-homo-19-nor-5α-pregn-17-en-20-one is hydrogenated in 80 ml. of dimethylformamide in the presence of 0.25 g. of palladium on charcoal (5%) until 1 millimole of hydrogen has been absorbed per millimole of compound. The reaction product is filtered off from the catalyst and the filtrate is concentrated under reduced pressure and poured into ice water. The Precipitate is filtered off, washed with water and taken up in methylene chloride. The methylene chloride solution is washed with water, dried and evaporated. The residue is chromatrographed on silica gel. After recrystallization from methylene chloride/hexane, 0.86 g. of 3β-hydroxy-D-homo-19-nor-5α-pregnan-20-one is obtained, which melts at 170-172° C.

Analogously, 3β-hydroxy-18-methyl-D-homo-19-nor-5α-pregnan-20-one is prepared from 3β-hydroxy- 18-methylestran-17-one via the intermediate stage of 3β-hydroxy-16α,17-methylene-18-methyl-19-nor-5α-pregnan-20-one by ring expansion and hydrogenation of the Δ$^{17}$-double bond.

EXAMPLE 1

7.5 g. of 3β-hydroxy-D-homo-5α-pregnan-20-one is dissolved in 140 ml. of tetrahydrofuran; 12.5 g. of triphenyl-phosphine and 8.2 g. of m-iodobenzoic acid are added to the reaction mixture, and 7.1 ml. of the diethyl ester of azodicarboxylic acid is added dropwise thereto under agitation. The reaction solution is further stirred for 20 minutes and then poured into 1 liter of ice water. The thus-precipitated product is filtered off, taken up in methylene chloride, washed with water, and evaporated under vacuum. The residue is chromatographed on silica gel, thus obtaining 13.5 g. of amorphous 3α-m-iodobenzoyloxy-D-homo-5α-pregnan-20-one.

13.5 g. of 3α-m-iodobenzoyloxy-D-homo-5α-pregnan-20-one is dissolved in 2400 ml. of methylene chloride; 8.4 g. of freshly prepared iodobenzene dichloride is introduced, and the reaction mixture is irradiated with three 300-watt "Comptalux" *) lamps for 10 minutes while argon is introduced.

*) internal mirror-coating sunlamp, Philips, Holland

Thereafter, the solution is concentrated under vacuum, dissolved in 1500 ml. of acetone, combined with a solution of 15.3 g. of silver perchlorate in 50 ml. of water, and agitated for 15 minutes. The thus-precipitated silver chloride is then vacuum-filtered, and the filtrate is concentrated under vacuum. The residue is taken up in ethyl acetate, washed with sodium chloride solution and water, dried over sodium sulfate, and concentrated by evaporation.

The thus-obtained crude 3α-m-iodobenzoyloxy-D-homo-5α-pregn-9(11)-en-20-one is heated under reflux in 500 ml. of methanol with 3 g. of potassium hydroxide for 3 hours. After neutralization with 4 ml. of glacial acetic acid, the solution is evaporated, taken up in ethyl acetate, washed with water, dried over sodium sulfate, and concentrated by evaporation. After chromatography and recrystallization from acetone-hexane, 4.9 g. of 3α-hydroxy-D-homo-5α-pregn-9(11)-en-20-one is obtained, m.p. 159°–160° C.

EXAMPLE 2

3.1 g. of 3α-hydroxy-D-homo-5α-pregn-9(11)-en-20-one is dissolved in 10 ml. of pyridine and 5 ml. of acetic anhydride, allowed to stand for 20 hours at room temperature, and then poured into ice water. The precipitate is vacuum-filtered, washed neutral, and dried. After recrystallization from acetone-hexane, 2.9 g. of 3α-acetoxy-D-homo-5α-pregn-9(11)-en-20-one is obtained, m.p. 138°–139° C.

EXAMPLE 3

Analogously to Example 1, the following compounds are prepared:

3.1 3α-Hydroxy-D-homo-19-nor-5αpregn-9(11)-en-20-one;
m.p. 142.5°–144° C., from 3β-hydroxy-D-homo-19-nor-5α-pregnan-20-one.

3.2 3α-Hydroxy-18-methyl-D-homo-19-nor-5α-pregn-9(11)-en-20-one;
m.p. 123°–125° C. (acetone-hexane), from 3β-hydroxy-18-methyl-D-homo-19-nor-5α-pregnan-20-one.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

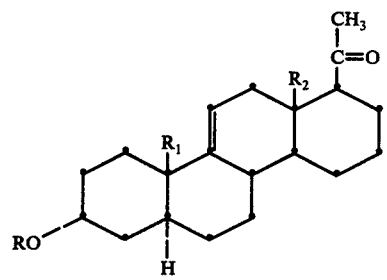

wherein, R is hydrogen, m-iodobenzoyl or the acyl radical of an alkanoic acid of 1–6 carbon atoms, $R_1$ is hydrogen or methyl and $R_2$ is methyl or ethyl.

2. A compound of claim 1 wherein $R_1$ is H.
3. A compound of claim 2 wherein $R_2$ is methyl.
4. A compound of claim 2 wherein $R_2$ is ethyl.
5. A compound of claim 1 wherein $R_1$ is methyl.
6. A compound of claim 5 wherein $R_2$ is methyl.
7. A compound of claim 5 wherein $R_2$ is ethyl.
8. A compound of claim 1, 3α-hydroxy-D-homo-5α-pregn-9(11)-en-20-one.
9. A compound of claim 1, 3α-hydroxy-D-homo-19-nor-5α-pregn-9(11)-en-20-one.
10. A compound of claim 1, 3α-hydroxy-18-methyl-D-homo-19-nor-5α-pregn-9(11)-en-20-one.
11. A compound of claim 1, 3α-acetoxy-D-homo-5α-pregn-9(11)-en-20-one.

* * * * *